US009109226B2

(12) United States Patent
Ong et al.

(10) Patent No.: US 9,109,226 B2
(45) Date of Patent: Aug. 18, 2015

(54) SYNTHETIC NUCLEIC ACIDS FOR POLYMERIZATION REACTIONS

(71) Applicant: New England Biolabs, Inc., Ipswich, MA (US)

(72) Inventors: Jennifer Ong, Salem, MA (US); Donald Johnson, Brookline, MA (US); Thomas C. Evans, Topsfield, MA (US); Lucia Greenough, Ipswich, MA (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 13/835,399

(22) Filed: Mar. 15, 2013

(65) Prior Publication Data

US 2013/0230887 A1 Sep. 5, 2013

Related U.S. Application Data

(63) Continuation-in-part of application No. 13/823,811, filed as application No. PCT/US2012/053330 on Aug. 31, 2012.

(60) Provisional application No. 61/623,110, filed on Apr. 12, 2012, provisional application No. 61/530,273, filed on Sep. 1, 2011, provisional application No. 61/605,484, filed on Mar. 1, 2012.

(51) Int. Cl.
*C12Q 1/68* (2006.01)
*C12N 15/113* (2010.01)
*C12N 9/12* (2006.01)

(52) U.S. Cl.
CPC ............ *C12N 15/113* (2013.01); *C12N 9/1252* (2013.01); *C12Q 1/6848* (2013.01)

(58) Field of Classification Search
None
See application file for complete search history.

(56) References Cited

U.S. PATENT DOCUMENTS

| 6,083,744 | A * | 7/2000 | Jennings et al. .............. 435/325 |
| 6,090,552 | A * | 7/2000 | Nazarenko et al. ........... 435/6.12 |
| 6,528,639 | B2 * | 3/2003 | Usman et al. ................. 536/24.5 |
| 6,777,180 | B1 * | 8/2004 | Fisher et al. .................. 435/6.16 |
| 2003/0165939 | A1 * | 9/2003 | Rabbani et al. .................... 435/6 |
| 2003/0180737 | A1 | 9/2003 | Gu et al. |
| 2006/0194225 | A1 * | 8/2006 | Spier .................................. 435/6 |
| 2007/0031857 | A1 * | 2/2007 | Makarov et al. ................... 435/6 |
| 2007/0141591 | A1 | 6/2007 | Borns |
| 2009/0142752 | A1 * | 6/2009 | Hall et al. .......................... 435/6 |
| 2011/0262898 | A1 | 10/2011 | Dong et al. |
| 2012/0142060 | A1 * | 6/2012 | Makarov et al. .............. 435/91.2 |
| 2013/0274135 | A1 * | 10/2013 | Zhang et al. ....................... 506/9 |
| 2014/0024033 | A1 * | 1/2014 | Jia et al. ........................ 435/6.11 |

FOREIGN PATENT DOCUMENTS

WO WO 9704131 A1 * 2/1997
WO WO2013033528 A1 3/2013

OTHER PUBLICATIONS

Bissler, DNA Inverted Repeats and Human Disease, Frontiers in Bioscience 3, d408-418, Mar. 27, 1998.*
Winter et al. (Many roads to maturity: microRNA biogenesis pathways and their regulation, Nature Cell Bio., vol. 11, No. 3, Mar. 2009, pp. 228-234).*
Lodish et al. (Micromanagement of the immune system by microRNAs, Nature Reviews Immunol., vol. 8, Feb. 2008, pp. 120-130).*
Kim (MicroRNA Biogenesis: Coordinated Cropping and Dicing, Nature Reviews Mol. Cell Bio., vol. 6, May 2006, pp. 376-385).*
Kawahara et al. (Redirection of Silencing Targets by Adenosine-to-Inosine Editing of miRNAs, Science 315, 1137 (2007)).*
Sakata et al. (Studies on the structure and stabilizing factor of the CUUCGG hairpin RNA using chemically synthesized oligonucleotides, Nucleic Acids Research, vol. 18, No. 13, Jun. 1990, pp. 3831-3839).*
Skerra (Phosphorothioate primers improve the amplification of DNA sequences by DNA polymerases with proofreading activity, Nucleic Acids Research, vol. 20, No. 14, Jul. 1992, pp. 3551-3554).*
Kramer (Stem-Loop RT-qPCR for miRNAs, in Current Protocols in Molecular Biology 15.10.1-15.10.15, Jul. 2011).*
Thelwell et al. (Mode of action and application of Scorpion primers to mutation detection, Nucleic Acids Research, 2000, vol. 28, No, 19, pp. 3752-3761).*
Carters et al. (Design and Use of Scorpions Fluorescent Signaling Molecules, in Methods in Molecular Biology, vol. 429: Molecular Beacons: Signalling Nucleic Acid Probes, Methods and Protocols, Ch. 8, 2008).*
ISR PCT/US2013/035217 dated Jul. 22, 2013.
Kellogg, et al. Biotechniques 16(6):1134-7 (1994).
Dang, et al. Journal of Molecular Biology 264(2):268-78 (1996).
Gill, et al., Nucleos. Nucleot. Nucleic Acids, 27:224-243 (2008).

(Continued)

*Primary Examiner* — Stephanie K Mummert
*Assistant Examiner* — Aaron Priest
(74) *Attorney, Agent, or Firm* — New England Biolabs, Inc.; Harriet M. Strimpel

(57) ABSTRACT

Compositions and methods are provided for inhibiting a polymerase from replicating non target DNA at a temperature below the amplification reaction temperature. The inhibitor is a synthetic nucleic acid which is single stranded but folds to form at least one double stranded region designed to melt at a temperature which is lower than the amplification reaction temperature, and at least one single stranded region where the single stranded region at the 5' end contains at least one uracil or inosine and optionally a sequence at the 3' end contains one or more derivative nucleotide or linkages.

16 Claims, 2 Drawing Sheets

(56) References Cited

OTHER PUBLICATIONS

Kim, et al., Bioanalysis, 3:227-239 (2001).
Nagamine, et al., Mol. Cel. Probes, 16:223-229 (2002).
Notomi, et al., Nucleic Acids research, 28:E63 (2000).
Nagamine, et al., Clin. Chem., 47:1742-1743 (2001).

* cited by examiner

US 9,109,226 B2

SYNTHETIC NUCLEIC ACIDS FOR POLYMERIZATION REACTIONS

CROSS REFERENCE

This application claims right of priority to provisional patent application Ser. No. US 61/623,110 filed Apr. 12, 2012 and is a continuation-in-part of U.S. patent application Ser. No. 13/823,811, filed Mar. 15, 2013.

BACKGROUND

Non-specific primer extension prior to reaction initiation in thermocycling DNA amplification reactions such as polymerase chain reaction (PCR), or isothermal DNA amplification reactions such as loop-mediated isothermal amplification (LAMP) may inhibit specific product formation, and lead to non-specific amplification and reaction irreproducibility. It is, therefore, desirable to block the activity of the polymerase, and hence primer extension, prior to reaction initiation. This has been achieved using antibodies (Kellogg, et al., *Biotechniques*, 16(6):1134-7 (1994)), affybodies (Affibody AB, Stockholm, Sweden), aptamers (Dang, et al., *Journal of Molecular Biology*, 264(2):268-78 (1996)), and chemical modification of the polymerase (U.S. Pat. No. 6,183,998). Although each of these techniques can be effective, they each have unique limitations. For example, preparation of antibodies requires use of animal systems, affybodies and aptamers require screening libraries of molecular variants, and chemical modifications require extra heat incubation steps to reverse the inactivating modification. It would be desirable to have a generalizable approach to rapidly and effectively create hot-start inhibitors targeted towards DNA polymerases.

SUMMARY

In general, in one aspect, a preparation is provided that includes: a synthetic single-strand nucleic acid having a 3' end and a 5' end, capable of forming a double-stranded region that extends from the 3' end and a single-stranded region having a 5' single-strand extension containing at least one uracil or inosine; and a buffer. An example of a synthetic single-strand nucleic acid is shown in FIG. 1.

Embodiments may include one or more of the following features: the at least one double-strand region has a melting temperature (Tm) of at least 10° C. less than a Tm for a target DNA in an amplification reaction, for example, below 90° C., 89° C., 88° C., 87° C., 86° C., 85° C., 75° C., 65° C., 55° C., 45° C. or 35° C.; a uracil or inosine is positioned at the fourth position in the 5' single-strand extension numbered from the 3'end; the synthetic nucleic acid is capable of forming a plurality of single-strand regions; a second single-strand region is a spacer; a third single-strand region forms a single-stranded loop at an internal location in the synthetic nucleic acid; the buffer may contain at least one of a polymerase, dNTPs, or primers; the spacer comprises hexa-ethylene glycol, a 3 carbon molecule or a 1',2'-dideoxyribose; the synthetic nucleic acid contains a derivative nucleotide and/or nucleotide linkage in a nucleic acid sequence at the 3' end where the derivative nucleotide may be selected from one or more inverted nucleotides, di-deoxynucleotides or amino-modified nucleotides; for example, the nucleotide linkage may be a phosphorothioate linkage;

In an embodiment, the preparation may additionally include one or more polymerases for example, one or more thermostable polymerases, for example at least one archaeal polymerase; a bacterial polymerase, and/or a variant of a wild type archaeal or bacterial polymerase. The synthetic nucleic acid and the polymerase may be present in a molar ratio of between 0.5:1 to 10:1.

In general in one aspect, a variant of a wild type polymerase includes at least 93% sequence identity to SEQ ID NO:25 and further includes at least one mutation at an amino acid position corresponding to 278, 307, and/or 402 in SEQ ID NO:25. In another aspects, mutations at 278, 307 and/or 402 may be inserted into any of the Bst polymerase variants described in U.S. application Ser. No. 13/823,811.

Embodiments may include one or more of the following features of the preparation: fusion of variant polymerase to a DNA binding domain such as Sso7d; and/or the variant polymerase optionally having an amino acid at one or more of the positions corresponding to 278, 307, and/or 402 that is not a histidine; for example where one or more mutations may be selected from a group of mutations corresponding to H278Q, H307R, H402Q.

In general in one aspect, a method is provided for inhibiting a polymerase extension reaction; that includes adding a preparation described above to a mixture containing a polymerase, a target DNA and dNTPs; and maintaining for a period of time prior to extension or amplification of the target DNA, the mixture at a temperature below the Tm of the double-stranded portion of the synthetic nucleic acid.

Embodiments may include one or more of the following features:

the at least one double-strand region has a Tm of at least 10° C. less than a Tm for a target DNA in an amplification reaction, for example, below 90° C., 89° C., 88° C., 87° C., 86° C., 85° C., 75° C., 65° C., 55° C., 45° C. or 35° C.; a uracil or inosine is positioned at the fourth position in the 5' single-strand extension numbered from the 3'end; the synthetic nucleic acid may include additional single-stranded nucleic acid regions such as a second single-strand region is a spacer; where for example, the spacer may include a hexa-ethylene glycol, a 3 carbon molecule or a 1',2'-dideoxyribose; and/or a third single-strand region forms a single-stranded loop at an internal location in the synthetic nucleic acid.

In an embodiment, the synthetic nucleic acid contains at least one derivative nucleotide and/or nucleotide linkage at the 3' end where the at least one derivative nucleotide may be selected from one or more inverted nucleotides, di-deoxynucleotides or amino-modified nucleotides; and for example, the at least one nucleotide linkage may be a phosphorothioate linkage.

In an embodiment, the one or more polymerases may include one or more thermostable polymerases, for example at least one archaeal polymerase; a bacterial polymerase, and/or a variant of a wild type archaeal or bacterial polymerase; and the synthetic nucleic acid and the polymerase may be present in a molar ratio of between 0.5:1 to 10:1.

In one embodiment, an additional step may be included of reversing the inhibition of the polymerase extension reaction by raising the reaction temperature above a Tm for the synthetic nucleic acid.

Figure 1:
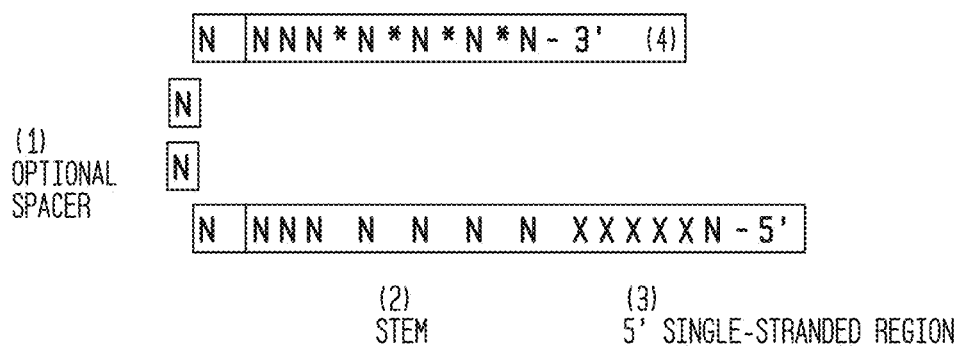
FIG. 1 shows a synthetic nucleic acid in the form of a hairpin oligonucleotide containing a 5' overhang, a 3' blocked end to prevent DNA polymerase extension and exonuclease cleavage and at least one non-standard base. (1) is the optional spacer; (2) is the double-stranded region or "stem"; (3) is the 5' single-strand; and (4) is the blocked 3' end: N=rNMP, dNMP or non-standard base; X=base that is recognized by the DNA polymerase uracil binding pocket; *=3' end modifications: phosphorothioate bonds and/or inverted base and/or dideoxynucleoside.

Lane 1 contains 2-log DNA ladder (New England Biolabs, Ipswich, Mass.), a MW marker for detection of 2 Kb amplicon.

Lane 2 contains 5 nM Archaeal Family B DNA polymerase without the synthetic nucleic acid present.

Lane 3 contains 5 nM Archaeal Family B DNA polymerase and 5 nM the synthetic nucleic acid, TM39U1G-Is.

Lane 4 contains 5 nM Archaeal Family B DNA polymerase and 5 nM the synthetic nucleic acid, TM39U1G-I*.

Lane 5 contains 5 nM Archaeal Family B DNA polymerase and 5 nM the synthetic nucleic acid, TM39U.

Lane 6 contains 5 nM Archaeal Family B DNA polymerase and 5 nM the synthetic nucleic acid, TM39Loop10T.

Lane 7 contains 5 nM Archaeal Family B DNA polymerase and 5 nM the synthetic nucleic acid, TM39U3-Is.

DETAILED DESCRIPTION OF THE EMBODIMENTS

Synthetic nucleic acids are described that reversibly inhibit polymerase extension reactions. These synthetic nucleic acid preferably contain at least one non-standard base (e.g. U or I) in a 5' single-strand overhang adjacent to a double-strand region. If the double-strand region is denatured into a single-strand or strands, the synthetic nucleic acid no longer blocks the polymerase from replicating substrate DNA. Preferably, inhibition of polymerase activity occurs at a first temperature that is at least 10° C. lower than a second temperature suitable for polymerase extension reactions. A polymerase extension reaction refers to the extension of a first single-strand nucleic acid by a polymerase where the extension is complementary to a second nucleic acid in association with the first strand.

In an embodiment, a synthetic nucleic acid is engineered so that the double-strand region melts at a desired temperature which is selected to melt at about 15° C. or 14° C. or 13° C. or 12° C. or 11° C. or 10° C. or 9° C. or 8° C. below polymerization extension conditions. Polymerase extension conditions include conditions for isothermal amplification occurring at for example 65° C. or a thermocycling amplification such as PCR which occurs at higher temperatures such as about 95° C. For example, the double-strand region in the synthetic nucleic acid may be designed to remain intact at a specific temperature in the range of −80° C. to 37° C. but become denatured at a specific temperature in a range of 37° C. to 100° C. The Tm of the synthetic nucleic acid can be modulated by one or more factors that include: changing the sequence or length of the double-strand region, changing the length of an internal single-strand region, adding mismatched or modified bases to the double-strand region, selecting a nucleotide composition having weaker base pairing properties such as an adenine, thymine or uracil rich sequence, or a sequence containing inosine, or abasic sites such as 1',2' dideoxyribose in a polymerization reaction buffer with a selected salt type (for example magnesium) and concentration. An example of a buffer is Thermopol® Buffer (New England Biolabs, Ipswich, Mass.).

In an embodiment of the invention, the design of a synthetic nucleic acid reversible inhibitor of polymerase extension reactions includes the following features: the synthetic nucleic acid can be DNA, DNA/RNA, RNA, or RNA/RNA; it can be formed from two single-strands or from a single nucleic acid (oligonucleotide) but should be capable of forming at least one double-strand region and a 5' single-strand overhang. It may optionally contain a plurality of single-strand regions and a plurality of double-strand regions. If the synthetic nucleic acid is an oligonucleotide, it should be capable of folding in such a way as to contain at least one double-strand region at a temperature lower than the reaction temperature as described above. The oligonucleotide may have a length in the range of 8-200 nucleotides. Any double-strand region in the inhibitor preferably has a length of 4-35 nucleotides.

The 5' single-strand overhang should be at least 4 nucleotides and preferably less than 100 nucleotides in length, for example 4-40 nucleotides, for example 6-10 nucleotides, and should contain one or more non-standard nucleotides such as U or I positioned between the second and tenth position of the overhang counted from the double-strand region, for example in the fourth position where the one or more non-standard nucleotides may be 1 to 5 uracils or 1 to 5 inosines. For example, the sequences shown in Table 1 were all found to be effective as reversible binding oligonucleotides.

In addition, a synthetic nucleic acid may optionally have a 3' end that is resistant to exonuclease activity and/or non-extendable by a polymerase. The 3' end of the oligonucleotide can be blocked from extension by modification, such as dideoxynucleotides, spacer molecules, inverted bases or amino-modified nucleotides. The 3' end can be made resistant to exonuclease degradation by the addition of phosphorothioate linkages between one or more bases at or near the 3' end or the use of inverted bases at the 3' end. The oligonucleotide can be made non-amplifiable by adding non-replicable bases in the internal sequence, such as carbon spacers, 1',2'-Dideoxyribose, abasic site, or thymine dimers.

Table 1 provides examples of synthetic nucleic acid molecules capable of forming hairpins and that were found to be effective in the assays described herein. The exemplified synthetic nucleic acid molecules have spacers of $T_n$ or $X_n$ where $T_{(4-9)}$ or $X_{(1-4)}$, a 5' end containing a modified base, $U_{(1-5)}$, or $I_{(1-3)}$ and has a U or an I at position 4 counted from the double-stranded region. The 5' end varies as shown.

TABLE 1

Oligonucleotides tested and effective in Hot Start PCR

Oligo Sequence containing uracil (U) or Inosine (I)
Length * = phosphorothioate bonds

| | |
|---|---|
| 28 | TUUUUUCTATCCTTATTTTTAAGGA*T*A*G (SEQ ID NO: 3) |
| 24 | TUUUUUAGCTAGGTTTTCCTA*G*C*T (SEQ ID NO: 4) |
| 24 | TUUUUUGCAGCGATTTTTCGC*T*G*C (SEQ ID NO: 5) |

TABLE 1-continued

Oligonucleotides tested and effective in Hot Start PCR

Oligo Sequence containing uracil (U) or Inosine (I)
Length * = phosphorothioate bonds

| Length | Sequence |
|---|---|
| 30 | TUUUUUGAGACTCGRCTTTTGACGAGT*C*T*C (SEQ ID NO: 6) |
| 34 | TUUUUUCTATCCTTAACGTTTTCGTTAAGGA*T*A*G (SEQ ID NO: 7) |
| 30 | TUUUUUACACTTCCGGTTTTCCGGAAG*T*G*T (SEQ ID NO: 8) |
| 31 | TUUUUUCTATCCTTAACGXCGTTAAGGA*T*A*G (SEQ ID NO: 9) |
| 34 | TUUUUUCTATCCTTAACGXXXXCGTTAAGGA*T*A*G (SEQ ID NO: 10) |
| 36 | TUUUUUCTATCCTTAACGTTTTTTCGTTAAGGA*T*A*G (SEQ ID NO: 11) |
| 40 | TUUUUUCTATCCTTAACGTTTTTTTTTCGTTAAGGA*T*A*G (SEQ ID NO: 12) |
| 34 | TUUUUUCTATCCTTAACTITTTTCGTTAAGGA*T*A*G (SEQ ID NO: 13) |
| 34 | TUUUUUCTATCCTTAACITTTTCGTTAAGG*A*T*A*G (SEQ ID NO: 14) |
| 34 | TUUUUUATCTCCTTAACITTTTCGTTAAGGAGAinvdT (SEQ ID NO: 15) |
| 34 | TUUUUUCTITCCTTIICGTTTTCGTTAAGGA*T*A*G (SEQ ID NO: 16) |
| 34 | TAUGGACTATCCTTAACGTTTTCGTTAAGGA*T*A*G (SEQ ID NO: 17) |
| 34 | TUUUGACTATCCTTAACGTTTTCGTTAAGGA*T*A*G (SEQ ID NO: 18) |
| 34 | TTITTTCTATCCTTAACGTTTTCGTTAAGGA*T*A*G (SEQ ID NO: 19) |
| 34 | TTITTTCTATCCTTAACGTTTTCGRRAAGG*A*T*A*G (SEQ ID NO: 20) |
| 34 | TTITTTATCTCCTTAACGTTTTCGRRAAGGAGAinvdT (SEQ ID NO: 21) |
| 34 | TIIITTCTATCCTTAACGTTTTCGTTAAGGA*T*A*G (SEQ ID NO: 22) |
| 34 | TIIITTCTATCCTTAACGTTTTCGTTAAGG*A*T*A*G (SEQ ID NO: 23) |
| 34 | TIIITTATCTCCTTAACGTTTTCGTTAAGGAGAinvdT (SEQ ID NO: 24) |

In an embodiment of the invention, one or more polymerases are added to the synthetic nucleic acid. The polymerases may be thermostable polymerases such as wild type or recombinant Archaeal DNA polymerases or bacterial DNA polymerases or variants (mutants) thereof including fusion proteins where the polymerase or variants thereof may be fused to a DNA binding domain such as Sso7d (for example, U.S. Pat. No. 7,666,645). A variant of a bacterial polymerase is exemplified at least 90%, 91%, 92% 93%, 95%, or 98% amino acid sequence homology or identity with SEQ ID NO:25 prior to fusion to a DNA binding domain if such is present. Regardless of the presence of an additional DNA binding domain, the variant preferably includes one or more mutations at positions corresponding to 52 (not R), 278, 307, 402, and/or 578 (not R) in SEQ ID NO:25, for example, one or more of the following mutations: H278Q, H307R, H402Q. Additional mutations may be optionally introduced into the polymerase by routine methods of random or directed mutagenesis.

Amplification procedures referred to herein include standard thermocycling or isothermal amplification reactions such as PCR amplification or LAMP (Gill, et al., *Nucleos. Nucleot. Nucleic Acids,* 27:224-43 (2008); Kim, et al, *Bioanalysis,* 3:227-39 (2011); Nagamine, et al., *Mol. Cel. Probes,* 16:223-9 (2002); Notomi, et al., *Nucleic Acids Res.,* 28:E63 (2000); and Nagamine, et al., *Clin. Chem.,* 47:1742-3 (2001)), helicase displacement amplification (HDA), recombinase polymerase amplification (RPA), nicking enzyme amplification reaction (NEAR) and/or strand displacement amplification (SDA). Variant polymerases described herein may be used in amplification or sequencing reactions with or without the use of synthetic nucleic acids described herein.

Amino Acid Sequence for a Wild Type Bst Polymerase (SEQ ID NO: 25)
AEGEKPLEEMEFAIVDVITEEMLADKAALVVEVMEENYHDAPIVGIALVN

EHGRFFMRPETALADSQFLAWLADETKKKSMFDAKRAVVALKWKGIELRG

VAFDLLLAAYLLNPAQDAGDIAAVAKMKQYEAVRSDEAVYGKGVKRSLPD

EQTLAEHLVRKAAAIWALEQPFMDDLRNNEQDQLLTKLEQPLAAILAEME

FTGVNVDTKRLEQMGSELAEQLRAIEQRIYELAGQEFNINSPKQLGVILF

EKLQLPVLKKTKTGYSTSADVLEKLAPHHEIVENILHYRQLGKLQSTYIE

GLLKVVRPDTGKVHTMFNQALTQTGRLSSAEPNLQNIPIRLEEGRKIRQA

FVPSEPDWLIFAADYSQIELRVLAHIADDDNLIEAFQRDLDIHTKTAMDI

FHVSEEEVTANMRRQAKAVNFGIVYGISDYGLAQNLNITRKEAAEFIERY

FASFPGVKQYMENIVQEAKQKGYVTTLLHRRRYLPDITSRNFNVRSFAER

TAMNTPIQGSAADIIKKAMIDLAARLKEEQLQARLLLQVHDELILEAPKE

EIERLCELVPEVMEQAVTLRVPLKVDYHYGPTWYDAK

All references cited herein are incorporated by reference.

Example

Assay to Measure Inhibition of Polymerase Activity Prior to PCR Cycling

Inhibition of polymerase activity was measured at a temperature below that used in the PCR assay which followed. The assay was performed as follows:

Primers were made for PCR to produce a 2 kb Lambda DNA amplicon. Additionally, the 3' end of the reverse primer contained 8 nucleotides that could anneal to Lambda DNA creating a false priming site producing a non-specific 737 bp amplicon.

The PCR assay was done in the presence of high levels of human genomic DNA and the reaction mixture was incubated with the thermostable polymerase at 25° C. for 15 minutes prior to PCR cycling. These conditions created many opportunities to form non-specific products. The presence of a nucleic acid composition to inhibit polymerase activity prior to amplification was required to yield a 2 kb amplicon, with minimal or no non-specific products. The reaction mix was set up on ice and contained the following reagents: Thermopol Buffer, 0.4 pg/μl Lambda DNA, 2.0 ng/μl Jurkat genomic DNA, 0.2 mM dNTP and 0.2 μM primers.

```
Forward primer, L30350F:
                                            (SEQ ID No: 1)
5'CCTGCTCTGCCGCTTCACGC3'

Reverse primer, L2kbalt4rv:
                                            (SEQ ID No: 2)
5'GGGCCGTGGCAGTCGCATCCC3'
```

Figure 2:
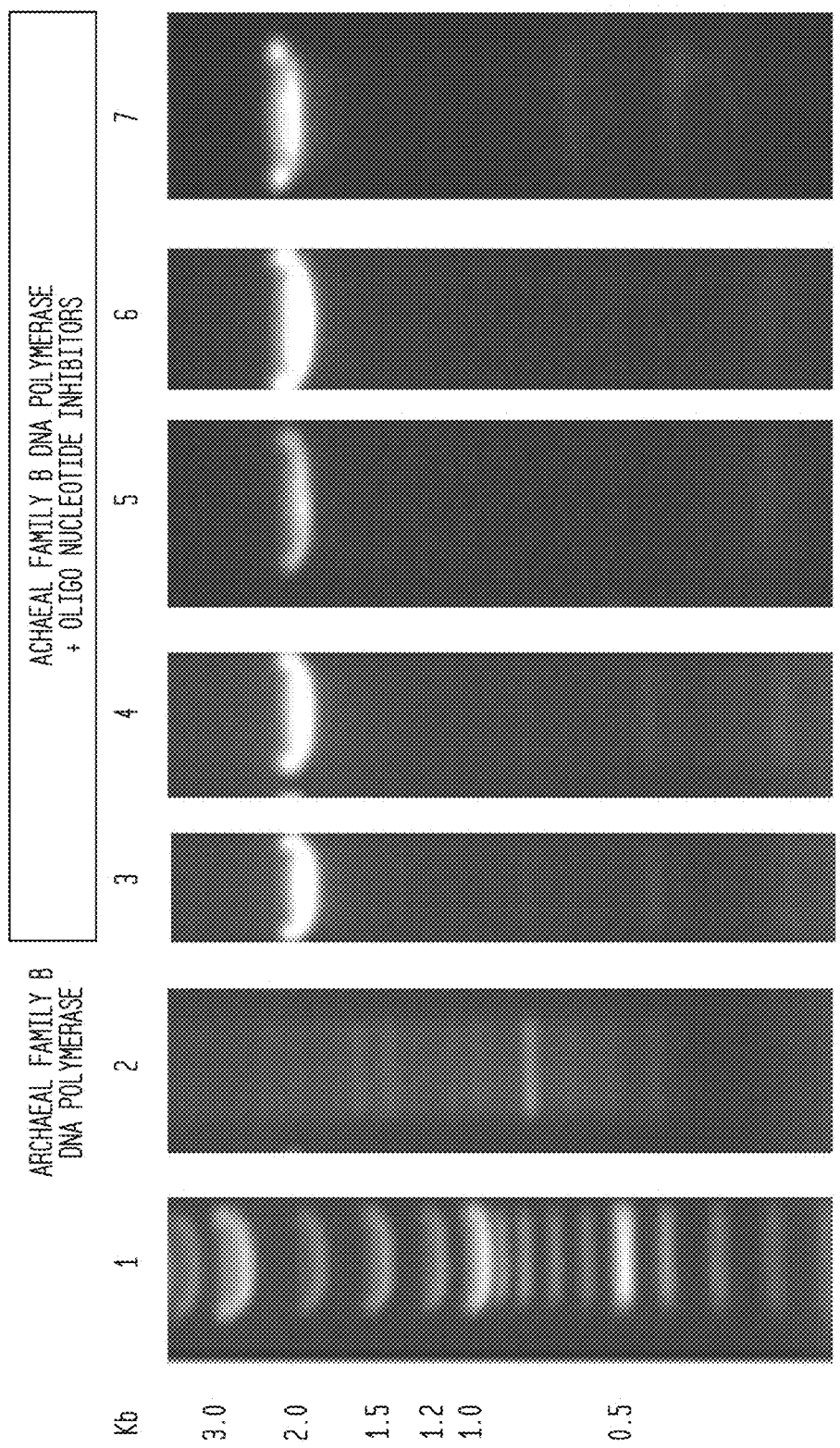
FIG. 2 shows a gel of the PCR products obtained with an Archaeal polymerase in the presence or absence of hairpin oligonucleotide inhibitors. In the absence of the hairpin oligonucleotide, the polymerase fails to amplify the expected 2 kb product. In the presence of the oligonucleotides the 2 kb product is amplified.

0.25 μl to 0.50 μl of 2.0 units/μl Vent® DNA Polymerase (NEB, Ipswich, Mass.) with or without the nucleic acid composition (see FIG. 2) was added to 25 μl or 50 μl of the reaction mix, and transferred to a PCR machine and cycled at 25° C. for 15-30 minutes, then cycled 35 times at 98° C. for 10 seconds, 45° C. for 20 seconds, 72° C. for 60 seconds, 72° C. for 4 minutes. DNA products generated by PCR cycling were analyzed by agarose gel electrophoresis.

In the absence of a reversibly inhibiting synthetic nucleic acid, the polymerase failed to yield the expected 2 kb Lamda amplicon. Non-specific products including the 737 bp amplicon were observed. In the presence of oligonucleotide inhibitors, a robust yield of the expected 2 kb Lambda amplicon was produced with minimal or no non-specific products.

---

What is claimed is:

1. An aqueous solution, comprising:
   (a) a thermostable polymerase that is active at a temperature of at least 65° C.; and
   (b) an oligonucleotide that has:
      (i) a double-stranded region having a $T_m$ of less than 65° C.,
      (ii) a 5' overhang comprising at least one uracil or inosine, and
      (iii) a modified nucleotide or linkage that makes the 3' end non-extendible or resistant to nuclease activity,
   wherein the oligonucleotide is capable of inhibiting the thermostable polymerase when the aqueous solution is at a temperature of below 37° C. but not at a temperature of 65° C. or greater.

2. The aqueous solution of claim 1, wherein the polymerase is a thermostable bacterial polymerase.

3. The aqueous solution of claim 1, wherein the polymerase is a thermostable archael polymerase.

4. The aqueous solution of claim 1, wherein the polymerase is a variant of a wild type thermostable polymerase.

5. The aqueous solution of claim 1, wherein the polymerase has an amino acid sequence that is at least 93% identical to SEQ ID NO:25.

6. The aqueous solution of claim 1, wherein the polymerase has an amino acid sequence that is at least 93% identical to SEQ ID NO:25 and comprises at least amino acid substitution at an position corresponding to 278, 307, and/or 402 in SEQ ID NO:25.

7. The aqueous solution of claim 1, wherein the oligonucleotide and the thermostable polymerase are present in the solution at a molar ratio of between 0.5:1 to 10:1.

8. The aqueous solution of claim 1, further comprising dNTPs and primers.

9. The aqueous solution of claim 1, wherein the double-stranded region is 4-40 nucleotides in length.

10. The aqueous solution of claim 1, wherein the double-stranded region is 6-60 nucleotides in length.

11. The aqueous solution of claim 1, wherein the uracil or inosine is positioned at the fourth position in the 5' single-strand overhang, numbered from the 3' end of single-stranded portion of 5' overhang.

12. The aqueous solution of claim 1, wherein the overhang comprises at least 2 uracils or inosines.

13. The aqueous solution of claim 1, wherein the oligonucleotide comprises a modified nucleotide that makes the 3' end not extendible.

14. The aqueous solution of claim 13, wherein the oligonucleotide comprises dideoxynucleotide, inverted base or amino-modified nucleotide at the 3' end.

15. The aqueous solution of claim 1, wherein the oligonucleotide comprises a linkage or modified nucleotide that makes the 3' end resistant to nuclease activity.

16. The aqueous solution of claim 15, wherein the oligonucleotide comprises a phosphorothioate linkage at or near the 3' end.

* * * * *

SEQUENCE LISTING

```
<160> NUMBER OF SEQ ID NOS: 25

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
cctgctctgc cgcttcacgc                                          20

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
gggccgtggc agtcgcatcc c                                        21

<210> SEQ ID NO 3
<211> LENGTH: 28
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (26)..(26)
<223> OTHER INFORMATION: phosphorothioate bond
<220> FEATURE:
<221> NAME/KEY: modified_base
<222> LOCATION: (27)..(27)
<223> OTHER INFORMATION: phosphorothioate bond
<220> FEATURE:
<221> NAME/KEY: modified_base
<222> LOCATION: (28)..(28)
<223> OTHER INFORMATION: phosphorothioate bond

<400> SEQUENCE: 3
```
tuuuuuctat ccttatttttt aaggatag                                   28

<210> SEQ ID NO 4
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (22)..(22)
<223> OTHER INFORMATION: phosphorothioate bond
<220> FEATURE:
<221> NAME/KEY: modified_base
<222> LOCATION: (23)..(23)
<223> OTHER INFORMATION: phosphorothioate bond
<220> FEATURE:
<221> NAME/KEY: modified_base
<222> LOCATION: (24)..(24)
<223> OTHER INFORMATION: phosphorothioate bond

<400> SEQUENCE: 4
tuuuuuagct aggttttcct agct                                        24

<210> SEQ ID NO 5
<211> LENGTH: 24
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (22)..(22)
<223> OTHER INFORMATION: phosphorothioate bond
<220> FEATURE:
<221> NAME/KEY: modified_base
<222> LOCATION: (23)..(23)
<223> OTHER INFORMATION: phosphorothioate bond
<220> FEATURE:
<221> NAME/KEY: modified_base
<222> LOCATION: (24)..(24)
<223> OTHER INFORMATION: phosphorothioate bond

<400> SEQUENCE: 5
tuuuuugcag cgattttttcg ctgc                                       24

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct
<220> FEATURE:
<221> NAME/KEY: modified_base
<222> LOCATION: (28)..(28)
<223> OTHER INFORMATION: phosphorothioate bond
<220> FEATURE:
<221> NAME/KEY: modified_base
<222> LOCATION: (29)..(29)
<223> OTHER INFORMATION: phosphorothioate bond
<220> FEATURE:
<221> NAME/KEY: modified_base
<222> LOCATION: (30)..(30)
<223> OTHER INFORMATION: phosphorothioate bond

<400> SEQUENCE: 6
tuuuuugaga ctcgrcttt gacgagtctc                                   30

<210> SEQ ID NO 7
<211> LENGTH: 34
<212> TYPE: DNA
<213> ORGANISM: Artificial Sequence

```
<220> FEATURE:
<223> OTHER INFORMATION: Synthetic construct
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 7
tuuuuuctat ccttaacgtt ttcgttaagg atag                          34

<210> SEQ ID NO 8
<211> LENGTH: 30
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (28)..(28)
<223> OTHER INFORMATION: phosphorothioate bond
<220> FEATURE:
<221> NAME/KEY: modified_base
<222> LOCATION: (29)..(29)
<223> OTHER INFORMATION: phosphorothioate bond
<220> FEATURE:
<221> NAME/KEY: modified_base
<222> LOCATION: (30)..(30)
<223> OTHER INFORMATION: phosphorothioate bond

<400> SEQUENCE: 8
tuuuuuacac ttccggtttt ccggaagtct                               30

<210> SEQ ID NO 9
<211> LENGTH: 31
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (19)..(19)
<223> OTHER INFORMATION: n represents any nucleotide
<220> FEATURE:
<221> NAME/KEY: modified_base
<222> LOCATION: (29)..(29)
<223> OTHER INFORMATION: phosphorothioate bonds
<220> FEATURE:
<221> NAME/KEY: modified_base
<222> LOCATION: (30)..(30)
<223> OTHER INFORMATION: phosphorothioate bonds
<220> FEATURE:
<221> NAME/KEY: modified_base
<222> LOCATION: (31)..(31)
<223> OTHER INFORMATION: phosphorothioate bonds

<400> SEQUENCE: 9
tuuuuuctat ccttaacgnc gttaaggata g                             31

<210> SEQ ID NO 10
<211> LENGTH: 34
<212> TYPE: DNA
<213> ORGANISM: Artificial Sequence
<220> FEATURE:
<223> OTHER INFORMATION: Synthetic construct
<220> FEATURE:
```

```
<221> NAME/KEY: misc_feature
<222> LOCATION: (19)..(22)
<223> OTHER INFORMATION: n represents any nucleotide
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 10
tuuuuuctat ccttaacgnn nncgttaagg atag                                    34

<210> SEQ ID NO 11
<211> LENGTH: 36
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (34)..(34)
<223> OTHER INFORMATION: phosphorothioate bond
<220> FEATURE:
<221> NAME/KEY: modified_base
<222> LOCATION: (35)..(35)
<223> OTHER INFORMATION: phosphorothioate bond
<220> FEATURE:
<221> NAME/KEY: modified_base
<222> LOCATION: (36)..(36)
<223> OTHER INFORMATION: phosphorothioate bond

<400> SEQUENCE: 11
tuuuuuctat ccttaacgtt ttttcgttaa ggatag                                  36

<210> SEQ ID NO 12
<211> LENGTH: 40
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (38)..(38)
<223> OTHER INFORMATION: phosphorothioate bond
<220> FEATURE:
<221> NAME/KEY: modified_base
<222> LOCATION: (39)..(39)
<223> OTHER INFORMATION: phosphorothioate bond
<220> FEATURE:
<221> NAME/KEY: modified_base
<222> LOCATION: (40)..(40)
<223> OTHER INFORMATION: phosphorothioate bond

<400> SEQUENCE: 12
tuuuuuctat ccttaacgtt tttttttcg ttaaggatag                               40

<210> SEQ ID NO 13
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n represents inosine
```

```
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 13
tuuuuuctat ccttaacnttt ttcgttaagg atag                              34

<210> SEQ ID NO 14
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n represents inosine
<220> FEATURE:
<221> NAME/KEY: modified_base
<222> LOCATION: (31)..(31)
<223> OTHER INFORMATION: phosphorothioate bond
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 14
tuuuuuctat ccttaacnttt ttcgttaagg atag                              34

<210> SEQ ID NO 15
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (18)..(18)
<223> OTHER INFORMATION: n represents inosine

<400> SEQUENCE: 15
tuuuuuatct ccttaacnttt ttcgttaagg agat                              34

<210> SEQ ID NO 16
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (9)..(9)
<223> OTHER INFORMATION: n represents inosine
<220> FEATURE:
<221> NAME/KEY: misc_feature
<222> LOCATION: (15)..(16)
```

-continued

```
<223> OTHER INFORMATION: n represents inosine
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 16
tuuuuuctnt ccttnncgtt ttcgttaagg atag                                 34

<210> SEQ ID NO 17
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 17
tauggactat ccttaacgtt ttcgttaagg atag                                 34

<210> SEQ ID NO 18
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 18
tuuugactat ccttaacgtt ttcgttaagg atag                                 34

<210> SEQ ID NO 19
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: n represents inosine
<220> FEATURE:
<221> NAME/KEY: modified_base
```

```
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 19
ttntttctat ccttaacgtt ttcgttaagg atag                                34

<210> SEQ ID NO 20
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: n represents inosine
<220> FEATURE:
<221> NAME/KEY: modified_base
<222> LOCATION: (31)..(31)
<223> OTHER INFORMATION: phosphorothioate bond
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 20
ttntttctat ccttaacgtt ttcgttaagg atag                                34

<210> SEQ ID NO 21
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (3)..(3)
<223> OTHER INFORMATION: n represents inosine
<220> FEATURE:
<221> NAME/KEY: modified_base
<222> LOCATION: (34)..(34)
<223> OTHER INFORMATION: inverted thymine

<400> SEQUENCE: 21
ttntttatct ccttaacgtt ttcgttaagg agat                                34

<210> SEQ ID NO 22
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: x represents inosine
<220> FEATURE:
```

<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 22
tnnnttctat ccttaacgtt ttcgttaagg atag                                34

<210> SEQ ID NO 23
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: n represents inosine
<220> FEATURE:
<221> NAME/KEY: modified_base
<222> LOCATION: (31)..(31)
<223> OTHER INFORMATION: phosphorothioate bond
<220> FEATURE:
<221> NAME/KEY: modified_base
<222> LOCATION: (32)..(32)
<223> OTHER INFORMATION: phosphorothioate bond
<220> FEATURE:
<221> NAME/KEY: modified_base
<222> LOCATION: (33)..(33)
<223> OTHER INFORMATION: phosphorothioate bond
<220> FEATURE:
<221> NAME/KEY: modified_base
<222> LOCATION: (34)..(34)
<223> OTHER INFORMATION: phosphorothioate bond

<400> SEQUENCE: 23
tnnnttctat ccttaacgtt ttcgttaagg atag                                34

<210> SEQ ID NO 24
<211> LENGTH: 34
<212> TYPE: DNA
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(4)
<223> OTHER INFORMATION: n represents inosine
<220> FEATURE:
<221> NAME/KEY: modified_base
<222> LOCATION: (34)..(34)
<223> OTHER INFORMATION: inverted thymine

<400> SEQUENCE: 24
tnnnttatct ccttaacgtt ttcgttaagg agat                                34

<210> SEQ ID NO 25
<211> LENGTH: 587
<212> TYPE: PRT
<213> ORGANISM: Bacillus stearothermophilus

<400> SEQUENCE: 25

Ala Glu Gly Glu Lys Pro Leu Glu Glu Met Glu Phe Ala Ile Val Asp
1               5                   10                  15

```
Val Ile Thr Glu Glu Met Leu Ala Asp Lys Ala Ala Leu Val Val Glu
             20                  25                  30
Val Met Glu Glu Asn Tyr His Asp Ala Pro Ile Val Gly Ile Ala Leu
         35                  40                  45
Val Asn Glu His Gly Arg Phe Phe Met Arg Pro Glu Thr Ala Leu Ala
     50                  55                  60
Asp Ser Gln Phe Leu Ala Trp Leu Ala Asp Glu Thr Lys Lys Lys Ser
 65                  70                  75                  80
Met Phe Asp Ala Lys Arg Ala Val Val Ala Leu Lys Trp Lys Gly Ile
                 85                  90                  95
Glu Leu Arg Gly Val Ala Phe Asp Leu Leu Ala Ala Tyr Leu Leu
                100                 105                 110
Asn Pro Ala Gln Asp Ala Gly Asp Ile Ala Ala Val Ala Lys Met Lys
            115                 120                 125
Gln Tyr Glu Ala Val Arg Ser Asp Glu Ala Val Tyr Gly Lys Gly Val
        130                 135                 140
Lys Arg Ser Leu Pro Asp Glu Gln Thr Leu Ala Glu His Leu Val Arg
145                 150                 155                 160
Lys Ala Ala Ala Ile Trp Ala Leu Glu Gln Pro Phe Met Asp Asp Leu
                165                 170                 175
Arg Asn Asn Glu Gln Asp Gln Leu Leu Thr Lys Leu Glu Gln Pro Leu
            180                 185                 190
Ala Ala Ile Leu Ala Glu Met Glu Phe Thr Gly Val Asn Val Asp Thr
        195                 200                 205
Lys Arg Leu Glu Gln Met Gly Ser Glu Leu Ala Glu Gln Leu Arg Ala
210                 215                 220
Ile Glu Gln Arg Ile Tyr Glu Leu Ala Gly Gln Glu Phe Asn Ile Asn
225                 230                 235                 240
Ser Pro Lys Gln Leu Gly Val Ile Leu Phe Glu Lys Leu Gln Leu Pro
                245                 250                 255
Val Leu Lys Lys Thr Lys Thr Gly Tyr Ser Thr Ser Ala Asp Val Leu
            260                 265                 270
Glu Lys Leu Ala Pro His His Glu Ile Val Glu Asn Ile Leu His Tyr
        275                 280                 285
Arg Gln Leu Gly Lys Leu Gln Ser Thr Tyr Ile Glu Gly Leu Leu Lys
290                 295                 300
Val Val Arg Pro Asp Thr Gly Lys Val His Thr Met Phe Asn Gln Ala
305                 310                 315                 320
Leu Thr Gln Thr Gly Arg Leu Ser Ser Ala Glu Pro Asn Leu Gln Asn
                325                 330                 335
Ile Pro Ile Arg Leu Glu Glu Gly Arg Lys Ile Arg Gln Ala Phe Val
            340                 345                 350
Pro Ser Glu Pro Asp Trp Leu Ile Phe Ala Ala Asp Tyr Ser Gln Ile
        355                 360                 365
Glu Leu Arg Val Leu Ala His Ile Ala Asp Asp Asn Leu Ile Glu
    370                 375                 380
Ala Phe Gln Arg Asp Leu Asp Ile His Thr Lys Thr Ala Met Asp Ile
385                 390                 395                 400
Phe His Val Ser Glu Glu Val Thr Ala Asn Met Arg Arg Gln Ala
                405                 410                 415
Lys Ala Val Asn Phe Gly Ile Val Tyr Gly Ile Ser Asp Tyr Gly Leu
            420                 425                 430
Ala Gln Asn Leu Asn Ile Thr Arg Lys Glu Ala Ala Glu Phe Ile Glu
```

```
                435                 440                 445
Arg Tyr Phe Ala Ser Phe Pro Gly Val Lys Gln Tyr Met Glu Asn Ile
    450                 455                 460

Val Gln Glu Ala Lys Gln Lys Gly Tyr Val Thr Thr Leu Leu His Arg
465                 470                 475                 480

Arg Arg Tyr Leu Pro Asp Ile Thr Ser Arg Asn Phe Asn Val Arg Ser
                485                 490                 495

Phe Ala Glu Arg Thr Ala Met Asn Thr Pro Ile Gln Gly Ser Ala Ala
            500                 505                 510

Asp Ile Ile Lys Lys Ala Met Ile Asp Leu Ala Ala Arg Leu Lys Glu
        515                 520                 525

Glu Gln Leu Gln Ala Arg Leu Leu Leu Gln Val His Asp Glu Leu Ile
    530                 535                 540

Leu Glu Ala Pro Lys Glu Ile Glu Arg Leu Cys Glu Leu Val Pro
545                 550                 555                 560

Glu Val Met Glu Gln Ala Val Thr Leu Arg Val Pro Leu Lys Val Asp
                565                 570                 575

Tyr His Tyr Gly Pro Thr Trp Tyr Asp Ala Lys
            580                 585
```